(12) United States Patent
Zart et al.

(10) Patent No.: US 7,175,482 B2
(45) Date of Patent: Feb. 13, 2007

(54) CONNECTOR ASSEMBLY FOR AN IMPLANTABLE MEDICAL DEVICE AND PROCESS FOR MAKING

(75) Inventors: Bryan J. Zart, Shakopee, MN (US); Brian R. Burwick, Guentersville, AL (US); Andrew J. Ries, Lino Lakes, MN (US); John E. Nicholson, Blaine, MN (US); Jay Lahti, Apple Valley, MN (US); Gregory A. Theis, St. Joseph, WI (US)

(73) Assignee: Medtronic, Inc., Minneapolis, MN (US)

( * ) Notice: Subject to any disclaimer, the term of this patent is extended or adjusted under 35 U.S.C. 154(b) by 291 days.

(21) Appl. No.: 10/966,636

(22) Filed: Oct. 15, 2004

(65) Prior Publication Data

US 2005/0137642 A1    Jun. 23, 2005

Related U.S. Application Data

(62) Division of application No. 09/885,354, filed on Jun. 20, 2001, now Pat. No. 6,817,905.

(60) Provisional application No. 60/212,746, filed on Jun. 20, 2000.

(51) Int. Cl.
*H01R 13/405* (2006.01)
*H05K 3/30* (2006.01)

(52) U.S. Cl. .................... 439/736; 29/841; 607/36; 607/37

(58) Field of Classification Search ............ 439/736, 439/387; 29/841, 825, 832; 607/36, 37; 264/36
See application file for complete search history.

(56) References Cited

U.S. PATENT DOCUMENTS

| 5,535,097 | A  | * | 7/1996 | Ruben et al. | 361/736 |
| 5,926,952 | A  | * | 7/1999 | Ito | 29/883 |
| 6,205,358 | B1 | * | 3/2001 | Haeg et al. | 607/36 |
| 6,219,913 | B1 | * | 4/2001 | Uchiyama | 29/883 |
| 6,601,296 | B1 | * | 8/2003 | Dailey et al. | 29/848 |
| 6,725,096 | B2 | * | 4/2004 | Chinn et al. | 607/115 |
| 6,878,013 | B1 | * | 4/2005 | Behan | 439/668 |

* cited by examiner

*Primary Examiner*—Michael C. Zarroli
(74) *Attorney, Agent, or Firm*—Michael C. Soldner; Girma Wolde-Michael

(57) ABSTRACT

A connector circuit assembly for use in an implantable medical device, and a method of making the assembly that includes a core portion formed of a thermoplastic material using either an injection molding process or a machining process. This core portion is adapted to be fitted with at least one electrically-conductive circuit component such as a connector member, a set-screw block, or a conductive jumper member. In one embodiment of the invention, the core portion includes multiple receptacles or other spaces that are adapted to be loaded with the various circuit components. The core assembly is positioned into a second-shot mold assembly, and a second thermoplastic material is injected into the mold so that the second thermoplastic material extends over and adheres to the core portion and the circuit component.

26 Claims, 12 Drawing Sheets

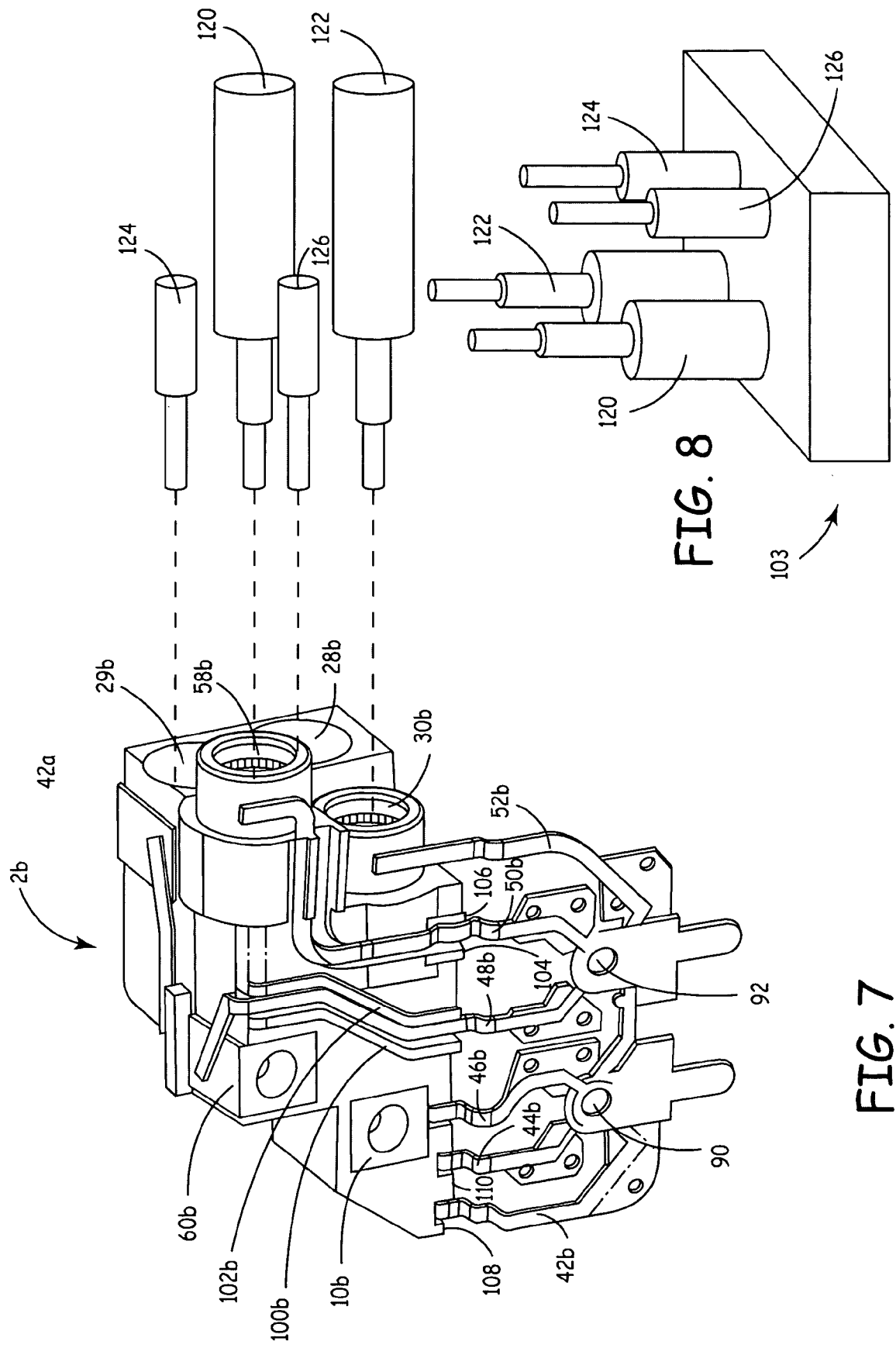

US 7,175,482 B2

CONNECTOR ASSEMBLY FOR AN IMPLANTABLE MEDICAL DEVICE AND PROCESS FOR MAKING

RELATED APPLICATIONS

This application is a divisional of application Ser. No. 09/885,354, filed Jun. 20, 2001 now U.S. Pat. No. 6,817,905, which claims priority to provisionally-filed patent application Ser. No. 60/212,746, filed Jun. 20, 2000.

FIELD OF THE INVENTION

This invention relates to a process for molding a circuit component; and more particularly, to a two-shot thermoplastic molding process for manufacturing an electrical connector.

BACKGROUND OF THE INVENTION

Electrical connectors and other similar electrical components often include electrical conductors embedded within an insulating housing to isolate the conductor from the surrounding environment. Embedding the conductor within a housing protects the conductor from damage, and also prevents the delivery of an electrical shock. Electrical isolation is particularly important when the connector is to be coupled to an implantable medical device such as a pacemaker or defibrillation system.

One way to form an electrical connector having conductors embedded therein is to mold a solid set-screw block using injection molding techniques. After the molding is completed, the surface of the set-screw block is formed to include channels. Wires or other types of connectors are pressed into the channels. Generally, each end of each wire is welded to some type of electrical contact. An insulating adhesive is then applied over the wires and channels. If the connector is to be used with an implantable medical device; a medical adhesive is often employed for this purpose. The adhesive is cured to form a protective, insulating layer that isolates the wires from external elements.

Although the afore-mentioned method is relatively straight-forward, it requires manual application of the adhesive. This introduces variables into the manufacturing process. If the adhesive is not properly dispensed, some portions of the conductor may become exposed. As a result, shorts may develop between adjacent conductors. Additionally, a conductor may come in contact with external elements, causing degradation and loss of conductive capabilities. Moreover, because a manual process is employed, the manufacturing mechanism is more time-consuming and expensive.

An alternative approach to the use of adhesives involves the positioning of one or more conductors within a mold in some predetermined orientation. An insulating plastic is then introduced into the mold to encapsulate the conductors. The plastic hardens to provide the necessary insulating layer around the conductors. While this process eliminates the variables associated with a manual step, it is nevertheless difficult to implement with other than a simple design. This is because the introduction of the plastic into the mold at high pressures generally causes the position of the conductors to shift. This may result in shorts between multiple conductors, or conversely, may result in loss of a desired electrical connection. While plastic injection systems of this nature generally include mechanisms to hold the conductors in place during the injection process, the process is more prone to failure than other methods because shifting of components may occur regardless of the efforts to prevent it. Additionally, a more complex tooling system is required to implement the process. Finally, the difficulty associated with maintaining isolation between multiple conductors places limits on the assembly dimensions. That is, an assembly cannot be made too small because shorts will occur between closely spaced conductors that shift during the mold injection process.

Yet another approach used to create connector assembly includes use of a two-step thermoset casting process. A first mold is used to receive a thermoset plastic material such as an epoxy. As is known in the art, a thermoset plastic hardens because of a chemical reaction occurring between the various components of the plastic material. After the curing process is complete, the first molded connector element is removed from the mold. Conductors are selectively positioned on the exterior of this first element. The first element is then positioned within a second mold and a thermoset material is selectively applied to the first element to encapsulate the conductors.

The two-step thermoset process provides a mechanism for embedding conductors within a connector in a more precise manner. This is because the first element holds the conductors in position while the second molding step is performed. However, because thermoset material requires a relatively long time to cure, the process is slow. The manufacture time is increased since two serial curing steps are required. Moreover, because the final products may not be removed from the molds until the curing is completed, many molds must be employed to increase output.

What is needed, therefore, is an improved mechanism for creating more complex connector structures using a faster production cycle.

SUMMARY OF THE INVENTION

The current invention provides an improved circuit assembly for use in an implantable medical device, and a method of making the assembly. The circuit assembly includes a core portion formed of a thermoplastic material using either an injection molding process or a machining process. This core portion is adapted to be fitted with at least one electrically conductive circuit component such as a connector member, a set-screw block, or a conductive jumper member. In one embodiment of the invention, the core portion includes multiple receptacles or other spaces that are adapted to be loaded with the various circuit components. Core portion may further be provided with groove and ridge members designed to position and retain conductive jumper members at predetermined locations at the surface of the core portion. Such conductive jumpers may be welded or soldered to a respective one of these circuit components to form electrical contacts between the jumpers and the respective circuit component.

After the electrically conductive circuit components are positioned in this manner with respect to the core portion, this core assembly is prepared for an overmolding process. This involves ensuring that certain portions of the core assembly will be protected from the flow of thermoplastic material during a subsequent overmold process. This process may include loading bushings into various connector members and/or set-screw blocks of the core element assembly.

When the core assembly has been prepared for the overmolding process, it is loaded into a second-shot mold. In one embodiment of the invention, the core assembly is aligned and retained within a cavity of the mold by utilizing slidable members that are provided by the mold, and that are adapted to engage the core assembly. Positioning of the core assembly within the mold cavity may further be accomplished using pegs that are adapted to engage various corresponding apertures of the core element assembly.

During the overmold process, a second-shot of thermoplastic material is injected into the mold. This thermoplastic material is heated to a temperature at, or above, the melting point of the material. This thermoplastic material is hot enough to create a bond between the core portion and the overmold material. To achieve this, the mass of the core element as compared to that of the overmold material is made as small as possible so that the heat energy from the mold is able to adequately heat the core portion. In one embodiment, the mass of the core portion is less than fifty percent of the mass of the overmold material, and preferably is less than thirty percent. Bonding may further be enhanced by providing ridges on the surface of the core portion that are melted during the overmold process and thereafter integrated with the overmold material. The bonding may also be facilitated by pre-heating the core portion prior to injecting the second shot of thermoplastic material into the mold.

In one embodiment of the invention, a hermetically-sealed connector assembly is provided for use with an implantable medical device (IMD) such as a cardioverter/defibrillator, a pacemaker, or any other type DME that is adapted to coupled to medical electrical leads. Because the connector assembly is manufactured using thermoplastic materials, the manufacturing process may be completed in a much shorter amount of time than similar assemblies formed of thermoset materials. The connector assembly includes one or more connectors that are adapted to couple mechanically and/or electrically to the pin or ring connectors of a medical electrical lead. Such connector members may conform to various standards for medical electrical leads, such as IS-1 and DF-1 standards.

Other aspects and advantages of the current inventive circuit assembly system and method of making the circuit assembly system will be apparent from the drawings and accompanying detailed description of the invention embodiments.

BRIEF DESCRIPTION OF THE DRAWINGS

FIG. 7 is a side perspective view of circuit member positioned on the surface of core element.

FIG. 8 is a front perspective view of an exemplary lead core assembly.

DETAILED DESCRIPTION OF THE INVENTION

Figure 1:
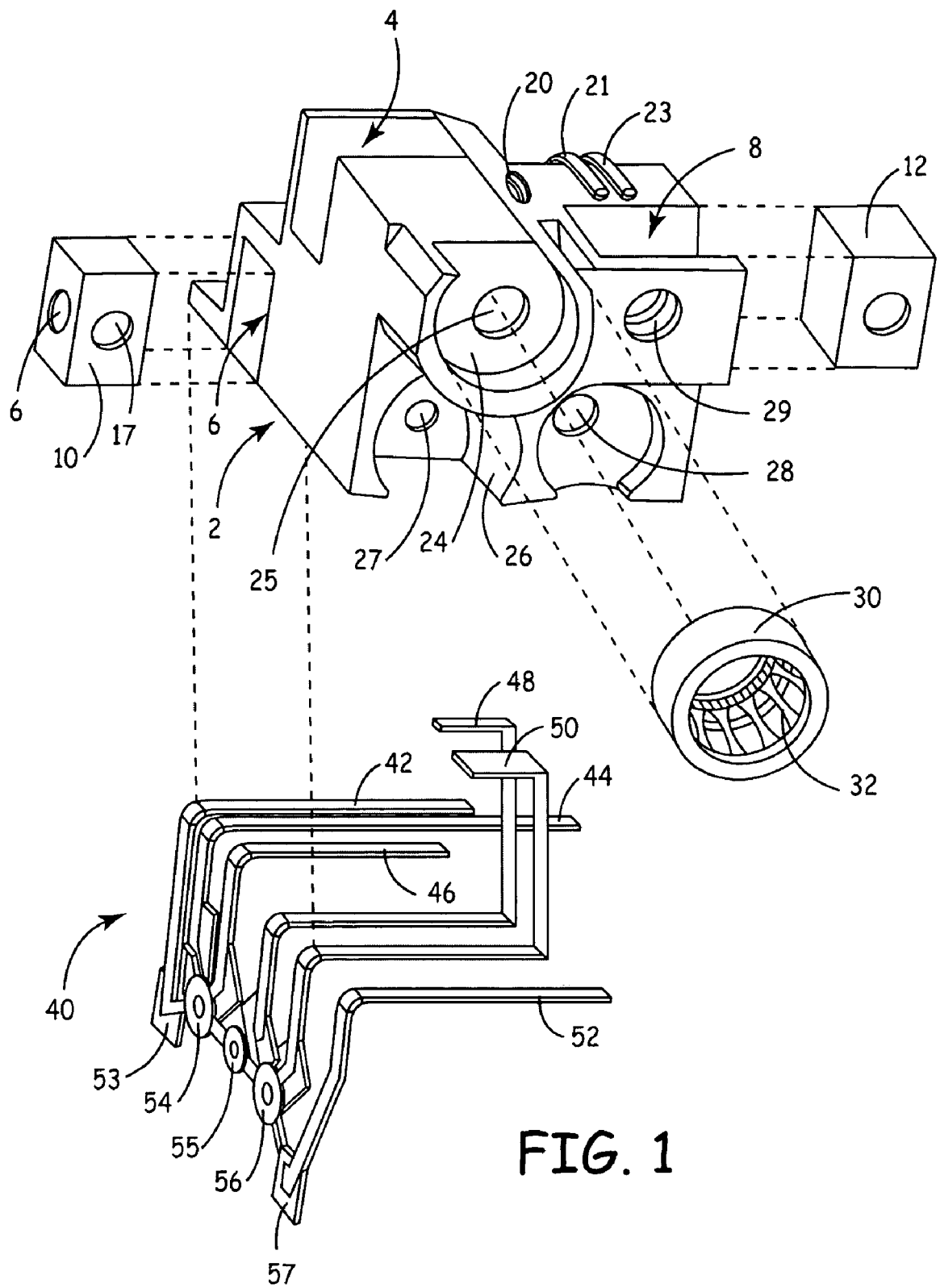
FIG. 1 is a front perspective view of a connector core element of one embodiment of the current invention.

FIG. 1 is a front perspective view of a connector core element 2 of one embodiment of the current invention. Core element is integrally formed of a biocompatible thermoplastic material, which may be a polyurethane such as pellathane commercially available from The Polymer Technology Group (PTG) Incorporated, or Tecothane® commercially available from Thermedics Incorporated. Other polyurethane materials are suitable for use in the current inventive process, as are other thermoplastic materials such as polysulfone. In one embodiment, a suitable biocompatible polyurethane may have a hardness of between 50 D and 90 D (Shore), and is preferably about 75 D.

The core element 2 is formed by heating the thermoplastic material to a temperature that is at, or slightly above, the melt point. The material is then injected into a primary mold formed into the desired shape of the core element and allowed to cool. Cooling is generally completed in between twenty to seventy seconds. This is much shorter than the curing period for thermoset materials, which may be as much as one hour. After cooling, core element 2 is removed from the mold. The removal process involves opening the mold, which includes an ejection mechanism that automatically releases the core element.

Core element 2 may take many different shapes. In one embodiment, core element includes a structure that supports various metal piece parts in a stable manner that can be maintained during a second-shot molding process to be discussed below. In the embodiment of FIG. 1, core element 2 includes receptacles 4, 6, and 8. Each of the receptacles is adapted to receive a respective set-screw block, such as set-screw block 10 to be inserted within receptacle 6, and 12 to be inserted within receptacle 8. Receptacle 4 is adapted to receive a similar set-screw block not shown in FIG. 1 for purposes of simplification. Set-screw blocks may be formed entirely, or partially, from a conductive material such as MP35N, stainless steel or titanium.

The set-screw blocks are loosely maintained within a respective receptacle by the shape of core element 2 until the second-shot over-molding process is completed. Each of these set-screw blocks includes an opening such as opening 16 to receive a set screw, and a second opening such as opening 17 to receive the pin or ring connector provided at the proximal end of a medical lead. A set screw inserted within opening 16 is used to mechanically couple to a lead connector pin or ring to hold the lead in place, as will be described further below.

In an alternative embodiment, the various receptacles needs not be included and the set-screw blocks may be integrally formed within the core element by positioning the set-screw blocks with the primary mold prior to injecting the thermoplastic material to form core element 2. In this instance, sealing means must be provided to prevent the thermoplastic from being injected into the openings of the set-screw blocks. For example, the primary mold could include peg members adapted to be loaded into the openings of set-screw blocks so that a tight seal is formed prior to injecting the thermoplastic into the mold. The pegs would also retain the set-screw blocks in position during the high-pressure injection process. Because of the complications associated with maintaining the set-screw blocks in position during the injection process, the former embodiment is preferred.

Returning to FIG. 1, the exemplary embodiment of core element 2 also includes additional circular receptacles 24 and 26. Each circular receptacle includes an aperture 25 and 27, respectively, to receive the connector pin of a medical electrical lead. For example, during use, a lead connector pin may be inserted within aperture 27 and further through opening 17. The lead is held in place by a fastening member inserted within opening 16 of set-screw block 10 and tightened on the lead pin or ring as is known in the art.

In the embodiment shown, each circular receptacle 24 and 26 is adapted to receive a respective connector member such as connector member 30. This type of connector member may be formed entirely or partially of a conductive material such as stainless steel or titanium. Connector member 30 is shown to include a multi-beam connector (MBC) 32 adapted to couple electrically and mechanically to a ring connector of a bipolar medical electrical lead. This type of connector member would support a lead having a connector conforming to the IS-1 standard, for example. Other types of connector members may be utilized to form an electrical and/or mechanical connection, as is known in the art.

In an alternative embodiment, the connector members may be eliminated by integrally forming the connectors such as connector member 30 within core element 2. This may be accomplished by loading the primary mold with the connectors prior to injecting the thermoplastic. As discussed above with respective to the set-screw blocks, some mechanism must be provided to prevent the thermoplastic from flowing over the conductive surface of the connectors. Additionally, the connector members must be retained in position during the high-pressure injection process. Because of the additional complexity associated with the need to maintain these components in position, the former embodiment of inserting these components into the completed core element 2 is preferred.

Core element 2 further includes additional lead bores 28 and 29 to receive the connector pins of additional leads. These lead bores may be adapted to couple to the pin of a lead conforming to the DF-1 standard for medical electrical leads, for example. Additional apertures such as apertures 20 may be provided to couple to additional circuit components in a manner to be discussed below. Core element may further have one or more guide members shown as guide members 21 and 23 integrally formed on the surface of core element 2. These guide members serve as support and positioning mechanisms for the additional circuit components, and also improves the overmolding process, as is described below.

FIG. 1 further illustrates a circuit member 40 which is formed of a conductive material such as stainless steel, titanium, niobium, tantalum, or any other conductive biocompatible conductive material. Circuit member 40 includes multiple conductive traces or finger elements 42 through 52, each extending to a respective connector pads 53 through 57. When the circuit member 40 is initially coupled to core member 2, connector pads may be electrically and mechanically joined to make the assembly process more efficient. Circuit member 40 may be soldered or welded to the various metal piece parts associated with core element 2, including set-screw blocks 10 and 12, and the various connector members 30 in a manner to be discussed below.

As noted above, using a single circuit member 40 having conductive finger elements that are mechanically and electrically joined makes the initial assembly process easier since multiple elements need not be loaded onto the core element 2. However, in this embodiment, an additional step is required later in the assembly process to electrically isolate these components, as will be discussed below. In another embodiment, each of the multiple conductive finger elements 42 through 52 may be an individual circuit element that is not mechanically or electrically coupled to the other finger elements. In this embodiment, the multiple finger elements must be individually loaded onto the core element. However, the additional step of electrically isolating these components later is not required. In yet another embodiment, the conductive finger elements may be joined in a single circuit member via insolated material. In this embodiment, the circuit member is a unified structure that couples the conductive finger elements mechanically, but provides electrical isolation. In this embodiment, the additional step of electrically isolating these components later is not required.

In yet another embodiment, the circuit member 40 could be integrally formed to include the various connector members and set-screw blocks so that the soldering or welding process may be eliminated. Using this embodiment, attaching the circuit member 40 to the core element involves loading the receptacles and apertures of the core element with the set-screw blocks and connector members, respectively.

Figure 2:
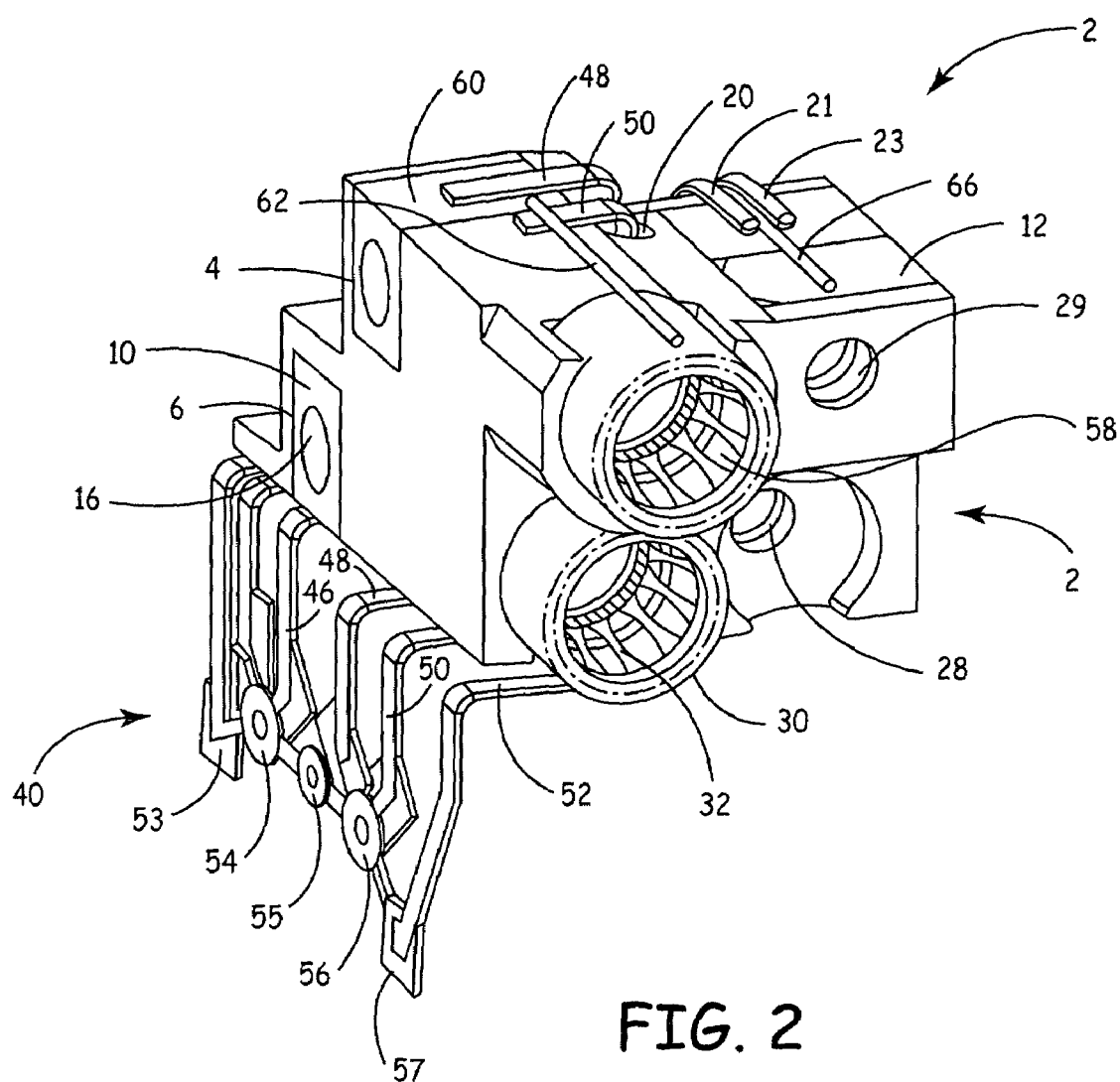
FIG. 2 is a front perspective view of a core member loaded with respective set-screw blocks and connector members.

FIG. 2 is a front perspective view of core member 2 with respective set-screw blocks inserted into receptacles 4, 6 and 8, and with connector members 58 and 30 inserted into circular receptacles 24 and 26. This view further illustrates circuit member 40 coupled to core member 2. In this embodiment, finger elements 48 and 50 of circuit member may extend through apertures provided within core element 2. For example, finger element 50 is inserted through aperture 20, which is a channel that extends through the core member. Similarly, finger element 48 extends through an additional aperture (not shown in FIG. 2) to position circuit member in a precise location with respect to core element 2. In one manner of use, finger elements 48 and 50 are formed of a material that is deformable, and which may be temporarily straightened to be threaded through a respective aperture such as aperture 20. In another exemplary embodiment, finger elements 48 and 50 are initially straight, and may be manually or automatically bent in the manner shown in FIG. 2 after being inserted within a respective aperture.

After circuit member 40 is coupled to core member 2, it may be soldered or welded to form predetermined electrical and mechanical connections between connector members and set-screw blocks and respective ones of the conductive finger elements. For example, finger element 46 may be coupled to set-screw block 10, whereas finger element 48 is electrically coupled to set-screw block 60.

Additional circuit elements may further be coupled to the core element using soldering, welding, or any other appropriate process. For example, jumper 62 may be soldered or welded to both finger element 46 and connector member 58 to form an electrical connection between the two components. Jumper 66 may be positioned on the surface of core member 2 using guide members 21 and 23 to align the circuit member in a desired location so that an electrical connection may be formed between set-screw block 12 and a predetermined respective one of the finger elements.

Figure 3:
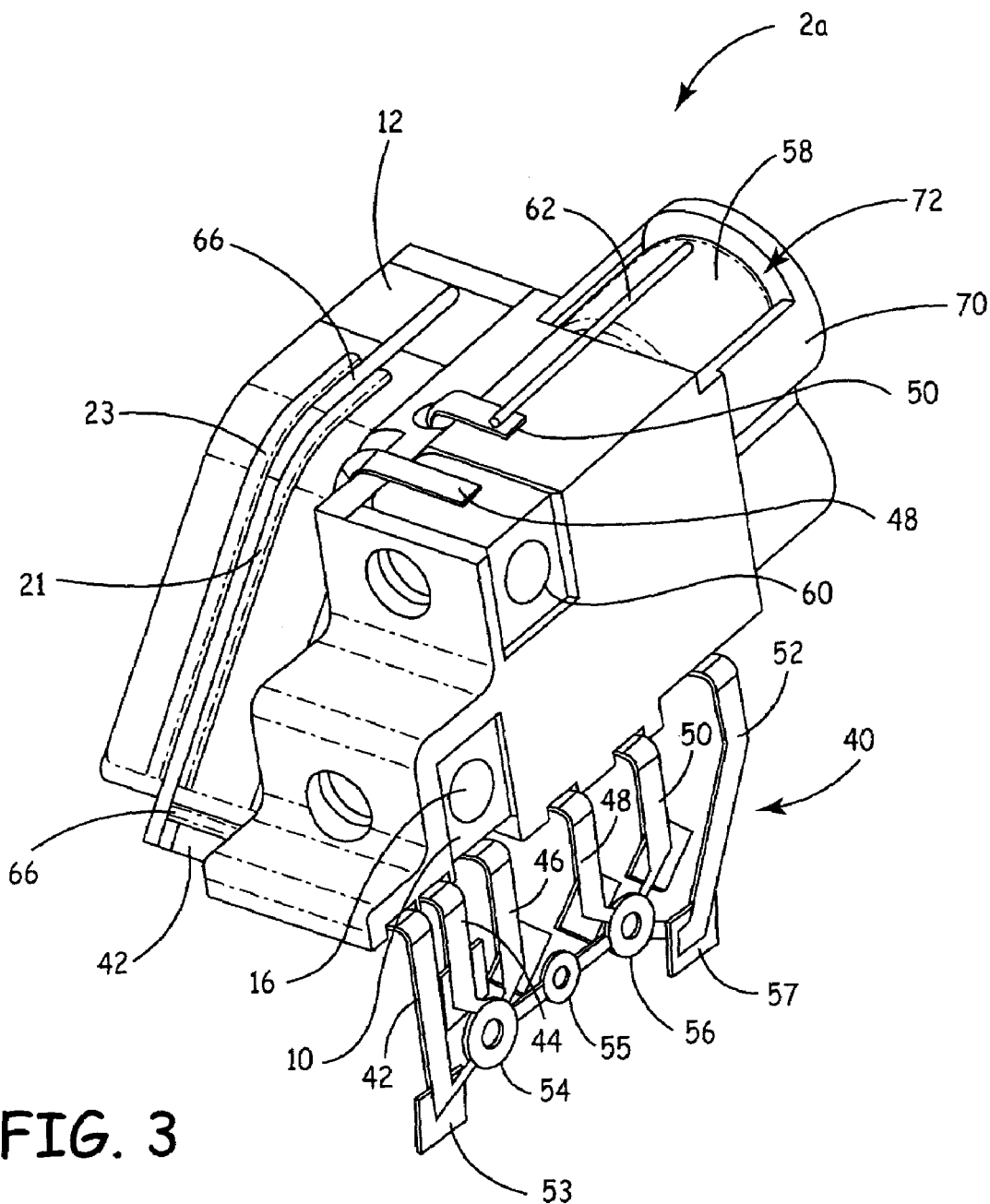
FIG. 3 is a back perspective view of an alternative embodiment of the core member.

FIG. 3 is a back perspective view of an alternative embodiment of the core member designated core member 2a. Although similar in almost every respect to the core members of FIGS. 1 and 2 discussed above, this core member includes a support structure 70 that is integrally molded into core element 2, and which is provided to receive and support connector members such as connector members 30 and 58. This support structure has a cutaway portion 72 to allow circuit element 62 to be welded or soldered to connector member 58. Although this support structure helps maintain the connector members in position during the second-shot overmolding process, it may make insertion of the connector members more cumbersome, and adds additional mass to the core element 2, which may be undesirable for reasons to be discussed further below.

FIG. 3 further illustrates the manner in which finger elements 48 and 50 of circuit member 40 are threaded through apertures of core member 2. Further illustrated is circuit element 66, which is maintained in position on the surface of core element by guide members 21 and 23 to form an electrical connection between set-screw block 12 and finger element 42.

Figure 4:
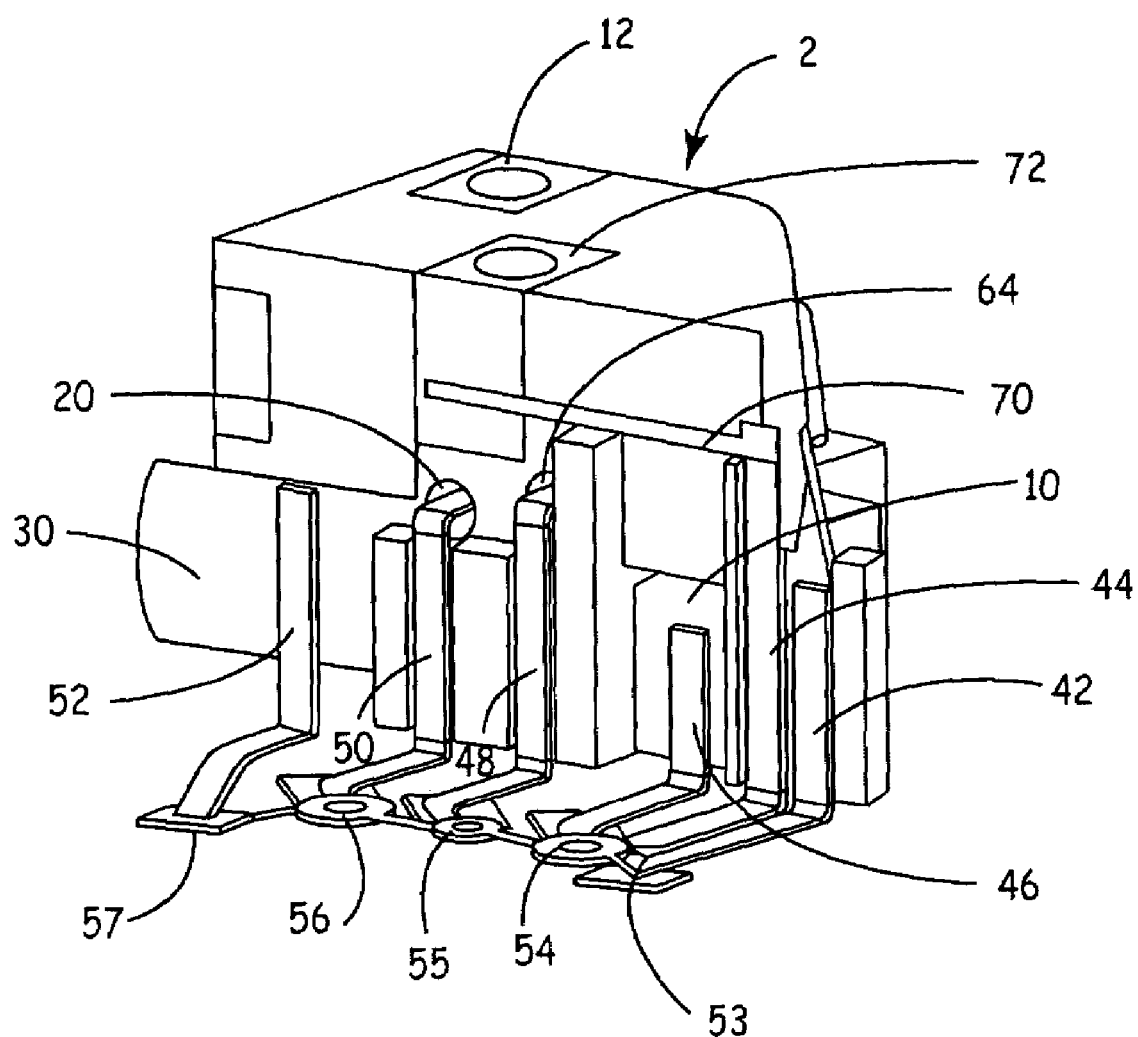
FIG. 4 is a bottom perspective view of core member.

FIG. 4 is a bottom perspective view of core member 2. This view illustrates the manner in which finger elements 48 and 50 extend through apertures 20 and 64, respectively. This view also shows the manner in which the various finger elements may be electrically coupled to connector members and set-screw blocks. For example, finger element 44 is jumpered via circuit element 70 to set-screw block 72; finger element 46 is electrically coupled to set-screw block 10, and so on.

As shown in FIG. 4, one manner of retaining circuit member 40 in position in proximity to core element 2 is through the use of apertures that extend through the core member and are adapted to receive respective finger elements of the circuit member 40. While this helps to prevent shifting of the circuit member 40 during the second-shot molding process, the process of threading the finger members through the various apertures is cumbersome and time-consuming.

Figure 5:
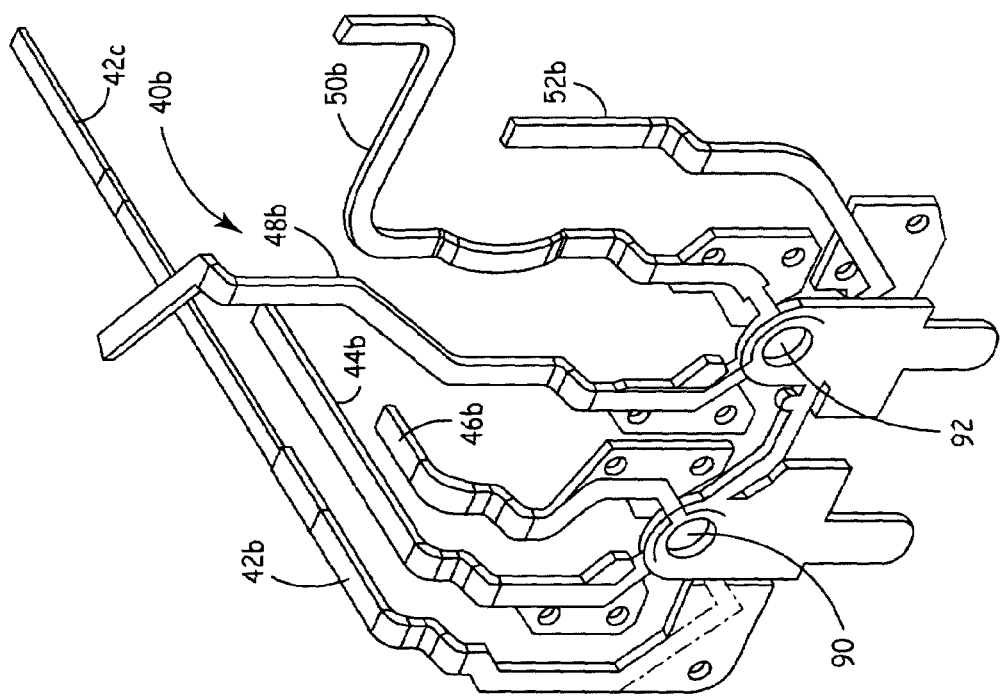
FIG. 5 is side perspective view of an alternative embodiment of the circuit member.

FIG. 5 is side perspective view of an alternative embodiment of the circuit member. In this view, like features of circuit member 40b as compared to circuit member 40 of FIGS. 1 through 4 are designated with like numeric identifiers including an additional suffix. This embodiment includes finger elements 44b through 46b that are not adapted to engage apertures in a core element. Instead, these elements are adapted to be placed externally on the surface of the core element to reduce assembly time prior to the second-shot overmolding step. One or more of the finger elements such as finger element 42b may have a longer, flexible conductive end. This end is adapted to be manually shaped to conform to a surface of the core member, as described below. FIG. 5 also illustrates the use of alignment apertures 90 and 92, which are provided to position the core element at a predetermined location within the second-shot mold to be discussed below.

Figure 6:
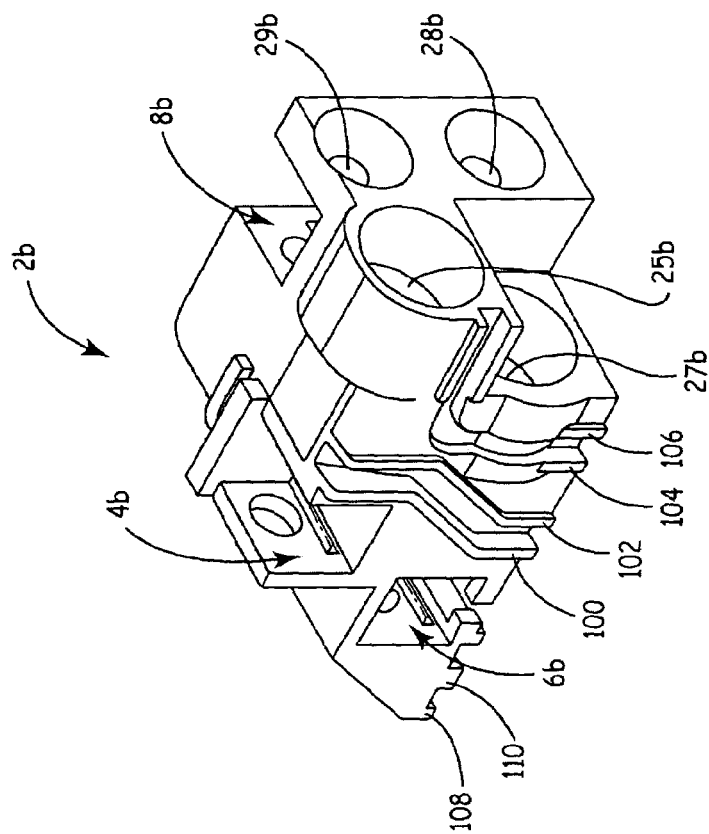
FIG. 6 is side perspective view of an alternative embodiment of the core element adapted to engage the circuit member of FIG. 5.

FIG. 6 is side perspective view of an alternative embodiment of the core element adapted to engage the circuit member 40b of FIG. 5. As in FIG. 5, like features of core element 2b as compared to core element 2 of FIGS. 1 through 4 are designated with like numeric identifiers including an additional suffix. Core element 2b includes channel guides such as channel guides 100 through 110 that are provided to guide the finger elements of circuit member 40b into the desired position on the surface of core element 2b. During the second-shot overmolding process, these channel guides retain the finger elements in position, and prevent shifting that may results in shorts between adjacent finger elements. These channel guides also promote integration of the material of the core element with the additional thermoplastic material provided during the overmolding process, as will be discussed further below.

FIG. 7 is a side perspective view of circuit member 40b positioned on the surface of core element 2b. This figure illustrates the manner in which finger elements are positioned using the guide members. For example, finger element 50b is positioned between guide members 104 and 106, and finger element 42b is positioned between guide members 108 and 110 provided on the bottom surface of core member 2b. The finger elements may be soldered or welded to the conductive components such as the set-screw blocks that are inserted in core member 2b in the manner discussed above. Other circuit elements may also be used to form electrical connections between circuit member 40b and a predetermined conductive component. Alternatively, the longer finger elements such a finger element 42b having a flexible elongated end 42c (FIG. 5) may be manually shaped into position and welded to form the desired connection as shown in FIG. 7. In this example, the end 42c of finger element 42b is shaped along the top surface of core member 2c to electrically couple to set-screw block 12c. This use of longer conductive finger elements makes the assembly process more efficient by eliminating the need for additional circuit components, and by minimizing the number of locations that must be welded or soldered.

After all conductive components have been inserted into the core element and the circuit member 40b has been welded, soldered, or otherwise fixed into place, the resulting core element assembly may be prepared to undergo the second-shot overmolding process. This preparation may involve inserting pin members into the connector members and the apertures of the set-screw blocks so that thermoplastic material does not fill these structures during the overmolding process. FIG. 7 illustrates pin members 120 and 122 being inserted into connector members 58b and 30b, respectively. Pin members 124 and 126 are similarly inserted into lead bores 29b and 28b, respectively. Additional pin members or bushings (not shown in FIG. 7 for clarity) may be inserted into the apertures of each of the set-screw blocks of core element 2b. These pin members are made of a material that will withstand the temperature and pressure conditions associated with the injection molding process. For example, the pin members may be made of a tool steel or another type of stainless steel. In one embodiment, multiple ones of the pin members may be incorporated into a core assembly structure to make insertion into the core element easier.

FIG. 8 illustrates an exemplary lead core assembly 130, which is assembly that provides the pin members 120 through 126 shown in FIG. 7. The lead core assembly aligns the pin members, and allows them to be inserted in one step.

In an alternative embodiment, ones of the pin members such as those inserted into the set-screw blocks may be eliminated by using protrusions in the second-shot mold assembly. These protrusions are inserted into the set-screw blocks as the core element is placed within the mold and the mold is closed, thereby eliminating the step of manually inserting the pin members into the core element. This is discussed further below.

Figure 9:
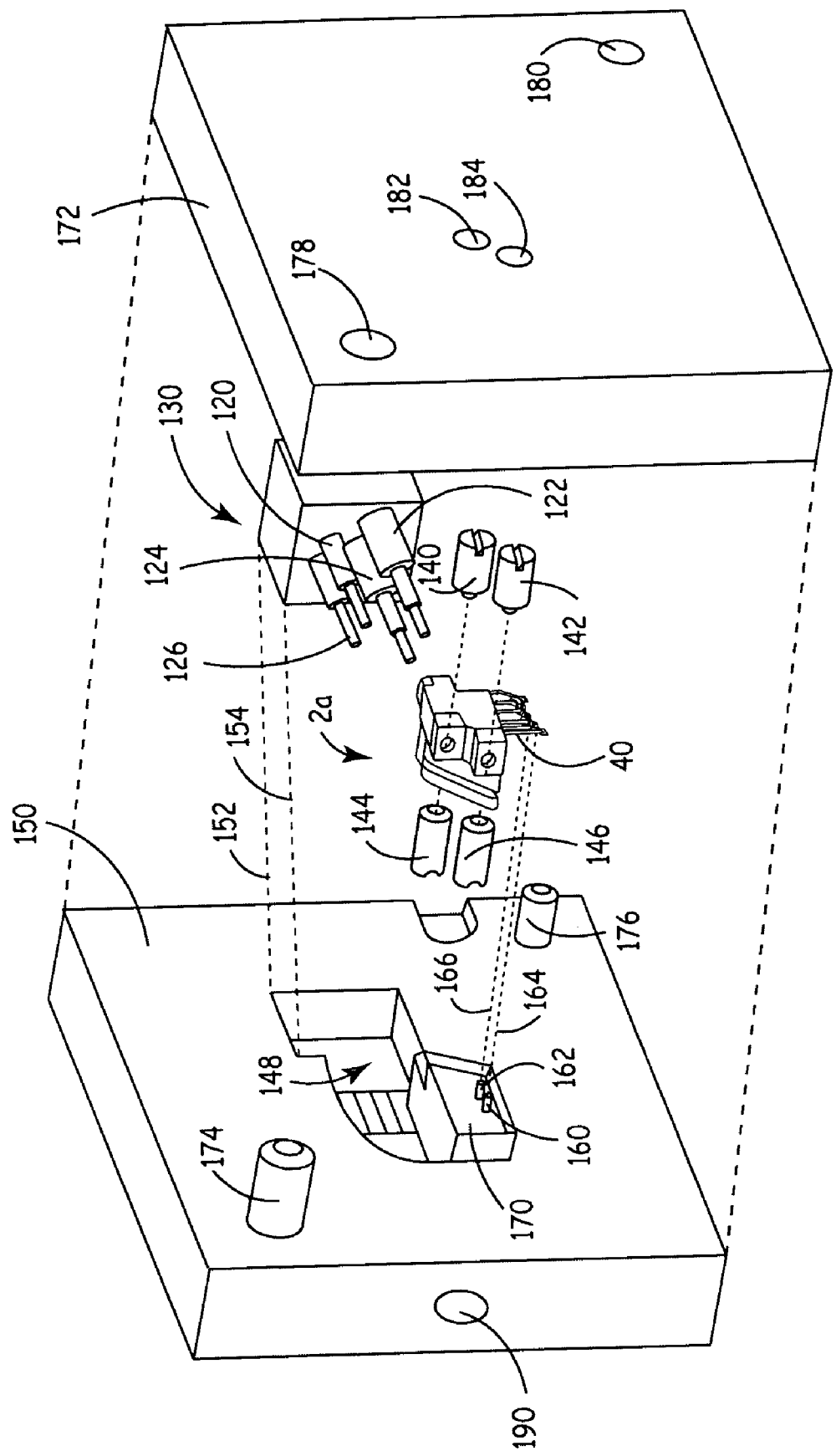
FIG. 9 is a perspective view of a core element being prepared for the overmolding process.

FIG. 9 is a perspective view of a core element being prepared for the overmolding process. This view, which is similar to that shown in FIG. 3, illustrates core member 2a and the associated metal piece parts that have been loaded into the core member. Lead core assembly 130 is utilized to insert pin members 120, 122, 124, and 126 into the respective structures of the core element as discussed in reference to FIG. 8. Similar bushings 140, 142, 144 and 146 may be inserted into the apertures of the set-screw blocks. As noted above, bushings 144 and 146 may be eliminated by instead providing protrusions within cavity 148 of the bottom portion 150 that are aligned with the set-screw blocks. Similar protrusions may be provided in the top portion 172 of the mold to replace bushings 140 and 142. Providing such structures in the mold itself eliminates the requirement of manually loading the bushings into the core element.

After the core element is prepared for the overmolding process, the entire assembly may then be loaded into cavity 148 of a bottom portion 150 of a second-shot mold fixture. The lead core assembly is positioned within the mold as shown by dashed lines 152 and 154. In this position, the lead core assembly suspends the core element within the cavity of the mold so that the surface of the core element is not in contact with the interior surface of the mold. The positioning of the core assembly may further be aided by fitting predetermined ones of the apertures included in the circuit member 40 with the alignment pins 160 and 162 of the mold as illustrated by dashed lines 164 and 166. For example, the apertures in connector pads 54 and 56 of circuit member 40 (FIGS. 2 and 3) or the alignment apertures 90 and 92 (FIG. 5) could be used for this purpose. The circuit member 40 may further be supported by a shoulder member 170.

After the assembly has been properly aligned within the bottom portion 150, the top portion 172 of the second-shot mold fixture is aligned with the bottom portion. This may be accomplished by inserting pegs 174 and 176 into channel members 178 and 180. Both top and bottom mold portions may include additional channels such as channels 182 and 184 to accommodate set-screws 140 and 142, respectively. Similar channels may be provided in the bottom portion 150 of the mold fixture.

When the bottom and top portions of the mold fixture have been aligned, a press may be utilized to maintain the alignment during the high-pressure injection procedure. A thermoplastic material is heated to at least the melting temperature, or preferably, slightly above the melting temperature, of the material, and is injected into cavity 148 via injection port 190. The same, or a different, thermoplastic material may be used in the second-shot injection process as compared to that used in the core element. Moreover, the second-shot material may entirely encapsulate the core element, or alternatively, need only cover a portion of the core element. For example, it may be desirable to leave exposed a portion of the thermoplastic material included in the core element in the region of the circuit member connector pads.

During the second-shot injection process, it is important to ensure that bonding occurs between the core element and the second shot material. If bonding does not occur, very small amounts of ionic liquid pool between the core element 2 and the overmold material after the connector has been implanted within a living body for an extended period of time. This may result in what is an unacceptably large leakage current between adjacent finger elements of the circuit element. One way to ensure that adequate bonding is achieved is to heat the second-shot plastic as hot as the material characteristics will allow, and to inject the material as quickly as possible. This allows the core element to be heated by, and thereafter bonded to, the second-shot material.

Another method used to enhance the bonding process is to ensure that the mass of the core element is as small as possible. This allows the core element to be heated sufficiently during the overmold process. In one embodiment, the mass of the thermoplastic material incorporated into the core element is less than half of the mass of the material utilized during the overmold process, and is preferably less than thirty percent of that of the overmold structure.

Another mechanism for enhancing the bonding of the core element to the overmold material involves heating the core element prior to injecting the second shot of thermoplastic material. If this method is utilized, the mass of the core element may be greater while still achieving adequate bonding. This is because the second shot of thermoplastic material is not providing all of the heat needed to warm the core element, with at least some of the heat being provided during the heating step that precedes the injection step. In one embodiment, the mass of the core element is greater than fifty percent of the thermoplastic material used during the overmold process while still retaining adequate bonding.

Integration of the core element with the overmold material may be further enhanced by providing relatively thin protruding structures to the core member surface. Because these relatively thin structures are readily melted and integrated with the second-shot material, integration of the core element with the overmold structure is enhanced. For example, guide members 100 through 110 (FIG. 6) serve not only to guide circuit elements on the surface of the core member, but also facilitate this type of bonding between the core element 2 and the overmold material. In one embodiment, additional thin fin-like structures may be provided in arbitrary shapes along various surfaces of the core member to facilitate additional integration. Such structures may be included in the first-shot mold assembly. Although such structures do enhance integration, the addition of such structures makes the molding of the core element more complex.

Following the injection of the overmold material, the entire assembly is allowed to cool for twenty to seventy seconds, depending on the type of thermoplastic material utilized as determined by the manufacturer specifications. The top portion of the mold is removed from the bottom portion, causing the finished connector assembly to be released. After removal from the mold, the connector pads of the circuit member 40 may be separated, if necessary, to achieve electrical isolation, as may be performed by cutting away the intervening conductive traces. The pads may then be soldered or welded to respective connectors of an implantable medical device such as a pacemaker or cardioverter/defibrillator, and overlaid with a medical adhesive to maintain electrical isolation in the connection area. It may be noted that if individual circuit elements are utilized in place of circuit member 40 or 40b, the step of removing the intervening conductive traces between finger elements may be eliminated.

Figure 10:
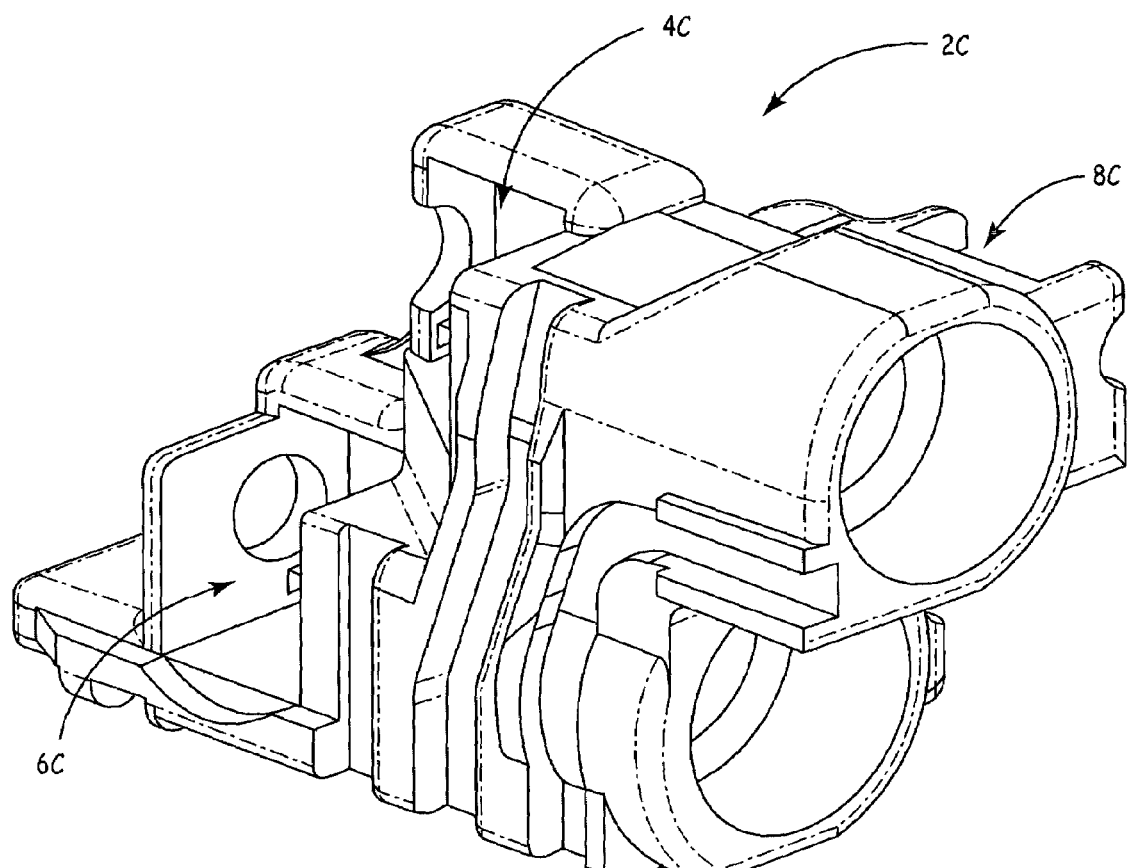
FIG. 10 is a side perspective view of an alternative embodiment of a core element which is designed to minimize core element mass.

As discussed in the foregoing paragraphs, one way to promote the formation of an adequate bond between the core member and the overmold material is to utilize a core element that is as small as possible. An alternative embodiment of a core element directed to minimizing core element mass is shown in FIG. 10. It may be noted that in this embodiment, the walls defining receptacles 4c, 6c, and 8c are relatively thin structures as compared to similar structures shown in FIGS. 1 and 6. Other structure adjacent to receptacle 8c has also been eliminated.

Figure 11:
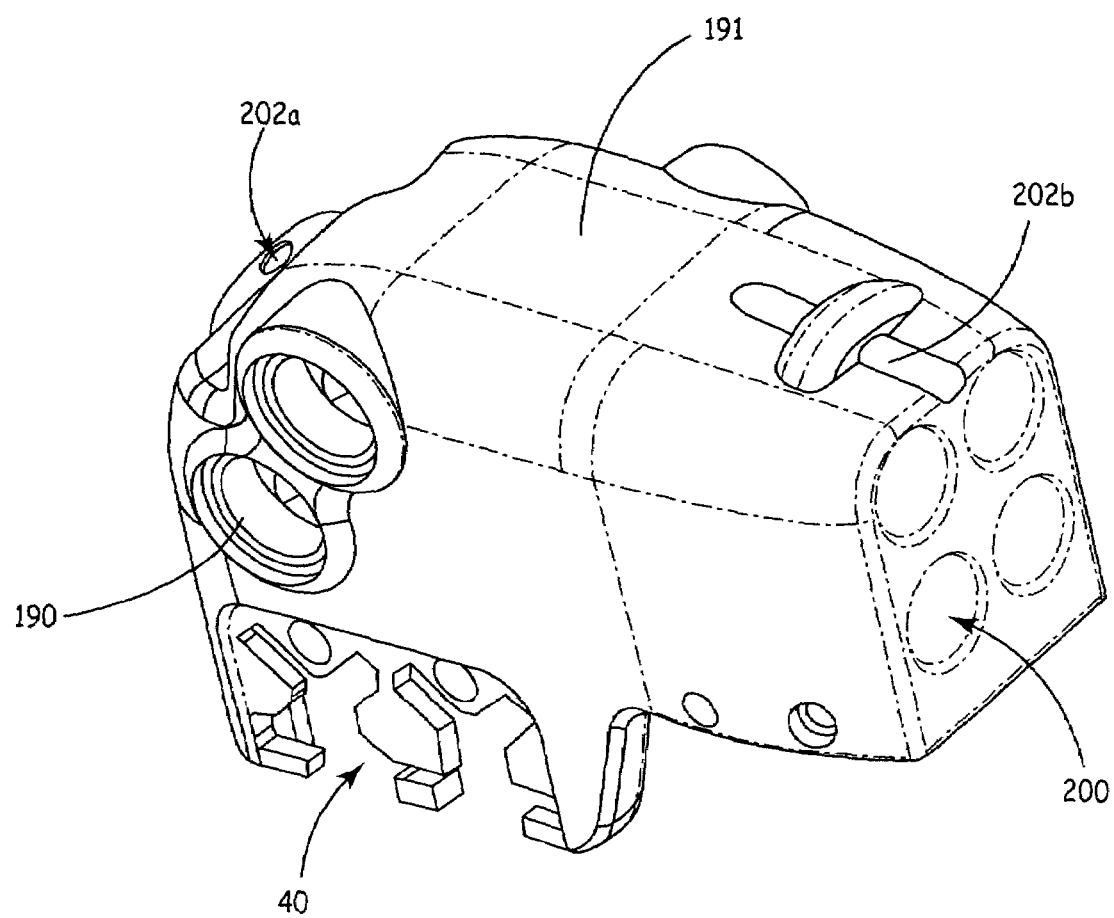
FIG. 11 is a perspective side view of an exemplary connector assembly formed after injection of the second-shot material.

FIG. 11 is a perspective side view of an exemplary connector assembly formed after injection of the second-shot material. The side view of FIG. 11 corresponds to the view of core element 2b in FIG. 6. Circuit member 40 has been trimmed in the manner discussed above to achieve the necessary isolation between pads. This view further illustrates an additional bore 190 extending through the second thermoplastic material 191, which may be integrally formed by a protrusion provided within the cavity of the bottom portion 150 or top portion 172 of the mold. This type of bore is provided to allow for tightening of the set-screws after a lead is insert into a respective lead receptacle such as receptacle 200 in this instance. This bore will be fitted with a stop member such as a grommet and/or a washer to form a fluid-tight opening that is adapted to receive a tool used during the tightening of the set-screw to the lead pin or ring connector. In one embodiment, other apertures 202a and 202b are provided to allow the connector to be sutured to tissue within the implant cavity. This type of aperture may be formed by a pin that extends between the bottom portion 150 and top portion 172 of the mold assembly.

Figure 12:
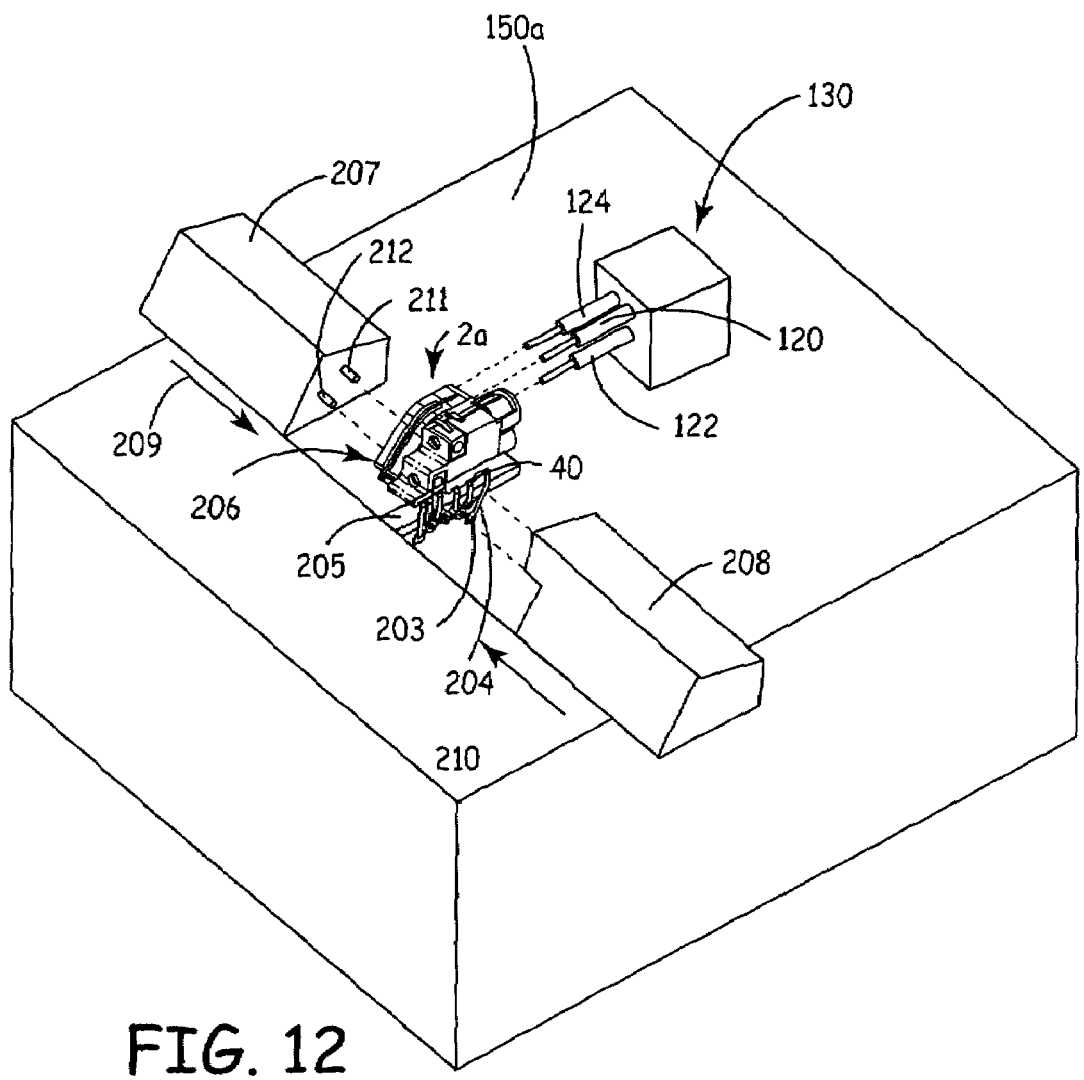
FIG. 12 is an alternative embodiment of the second-shot mold assembly of FIG. 9.

FIG. 12 is an alternative embodiment of the second-shot mold assembly of FIG. 9. This view illustrates core element 2a, the associated metal piece parts that have been loaded into the core member, and circuit member 40. This loaded core element assembly is then positioned in the bottom portion 150a of the second-shot mold fixture. In a manner similar to that discussed above with respect to FIG. 9, apertures provided within the circuit element may be positioned over pins 203 and 204 of shoulder member 205 to properly align and suspend core member over cavity 206 of the mold. Two slidable members 207 and 208 are provided to move into position around the core element assembly, as shown by arrows 209 and 210, respectively. These slidable members may be adapted to slide within tracks of the bottom portion 150a. Each of the slidable members includes one or more pegs such as pegs 211 and 212 of slidable member 207 to engage the set-screw block apertures so that additional bushings 140 through 146 (FIG. 9) are not needed. The slidable members provide additional stability during the second-shot injection mold process, and make removal of the connector assembly following the second-shot injection process less difficult.

Also shown in FIG. 12 is lead core assembly 130, which may be slidably positioned within the bottom portion 150a of the mold as illustrated by arrow 211 to engage the connector members of the core element 2a in the manner discussed above. Once the lead core assembly 130 and slidable members 207 and 208 are in position, a top portion of the mold which is similar to top portion 172 (FIG. 9) may be positioned over the bottom portion 150a. This top portion is held in position by a press or other mechanism during the second-shot injection process, as discussed above.

Figure 13:
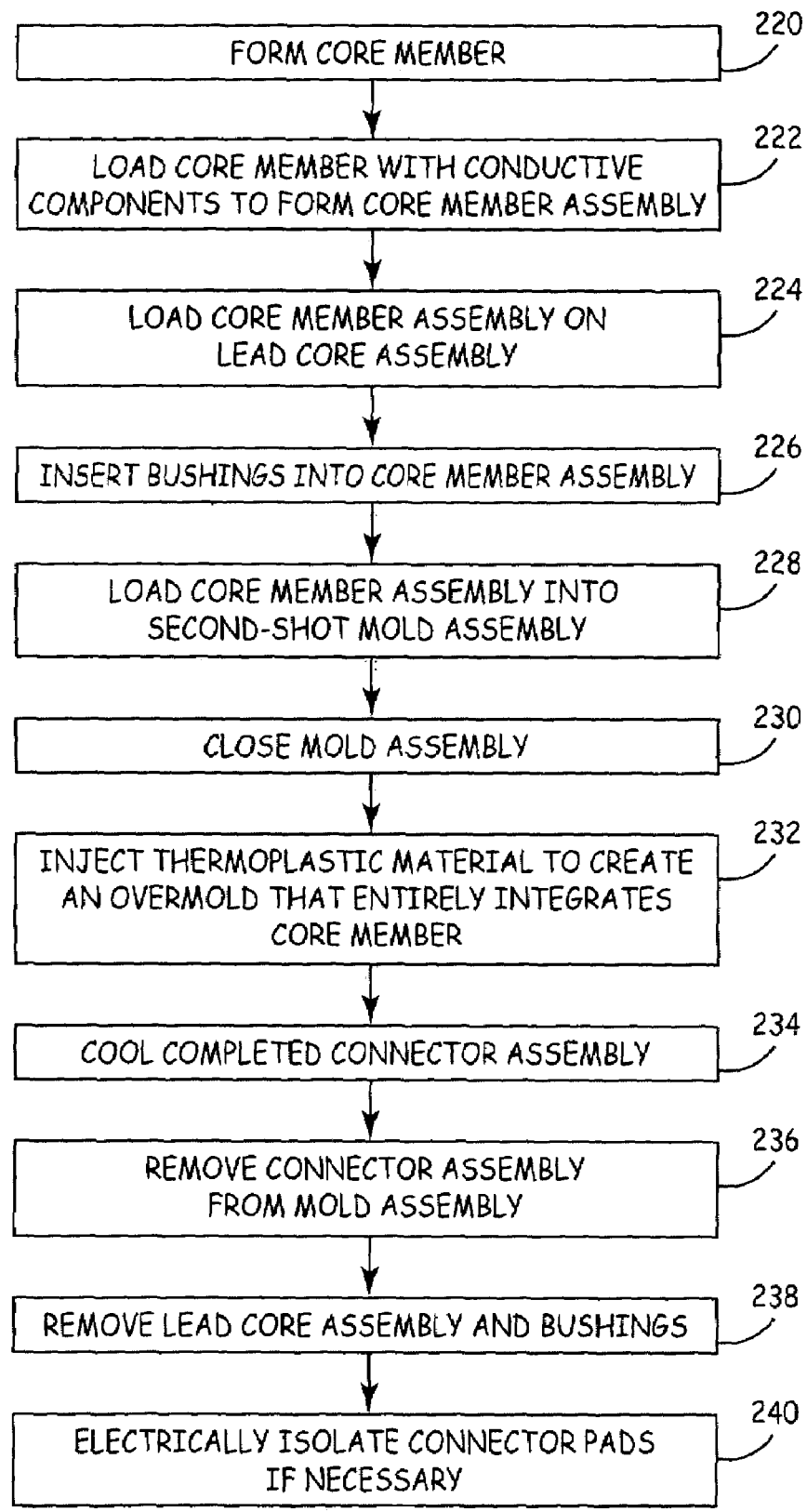
FIG. 13 is a flowchart of the inventive assembly process.

FIG. 13 is a flowchart indicating the steps utilized to make the current exemplary connector assembly. Although for discussion purposes the associated description involves the core element of FIG. 1, it will be understood the described process is equally applicable to the production of any connector type, or an entirely different type of thermoplastic component. In step 220, core member 2 is created. This may be accomplished by injecting a thermoplastic material into a primary mold assembly, or by fabricating a core member such as by a machining process. In step 222, the core member is loaded with the various conductive components such as the set-screw blocks and connector members to form the core member assembly. This step includes welding or solder the circuit member 40 to the various other conductive components. Processing continues with step 224, wherein the core member assembly is loaded onto the lead core assembly. Additional bushings may be inserted into set-screw blocks in 226 to ensure these structures remain open during the overmolding process, although this step is unnecessary if protrusions adapted to be inserted in the set-screw blocks are included in the second-shot mold assembly.

Next, in step 228, the core member assembly is loaded into the bottom portion 150 of the second-shot mold assembly. If desired, apertures in the circuit member 40 may be used to align the core member assembly within the mold cavity in a manner discussed above. The top portion 172 of the mold assembly is positioned over the bottom portion 150 as indicated by step 230, and the two portions are held together using a press, for example. Processing continues with step 232, wherein the thermoplastic material is injected to create the overmold. To bond the core member 2 with the overmold material, it is critical to heat the core member adequately. This may be accomplished by ensuring the mass of the core member is as small as possible as compared to the mass of the overmold material. In one embodiment, the mass of the core element is less than fifty percent of the mass of the overmolding material, and is preferably less than thirty percent of the overmold mass, as is discussed above. The bonding process may further be enhanced by pre-heating the core element prior to the overmold process, or by utilizing a thermoplastic material that can be heated to a relatively high temperature without altering the material characteristics. In either of these instances, the core element may have a mass that is greater than fifty percent of the overmold process while still achieving adequate bonding.

The connector assembly is cooled in step 234, and then removed from the mold assembly in step 236. The lead core assembly and optional bushings may be removed in step 238, and the various connector pads of the circuit member may be electrically isolated, as by removing interconnecting ones of the conductive traces. This is illustrated in step 240. As noted above, if individual circuit elements are used, this step is not needed.

Figure 14:
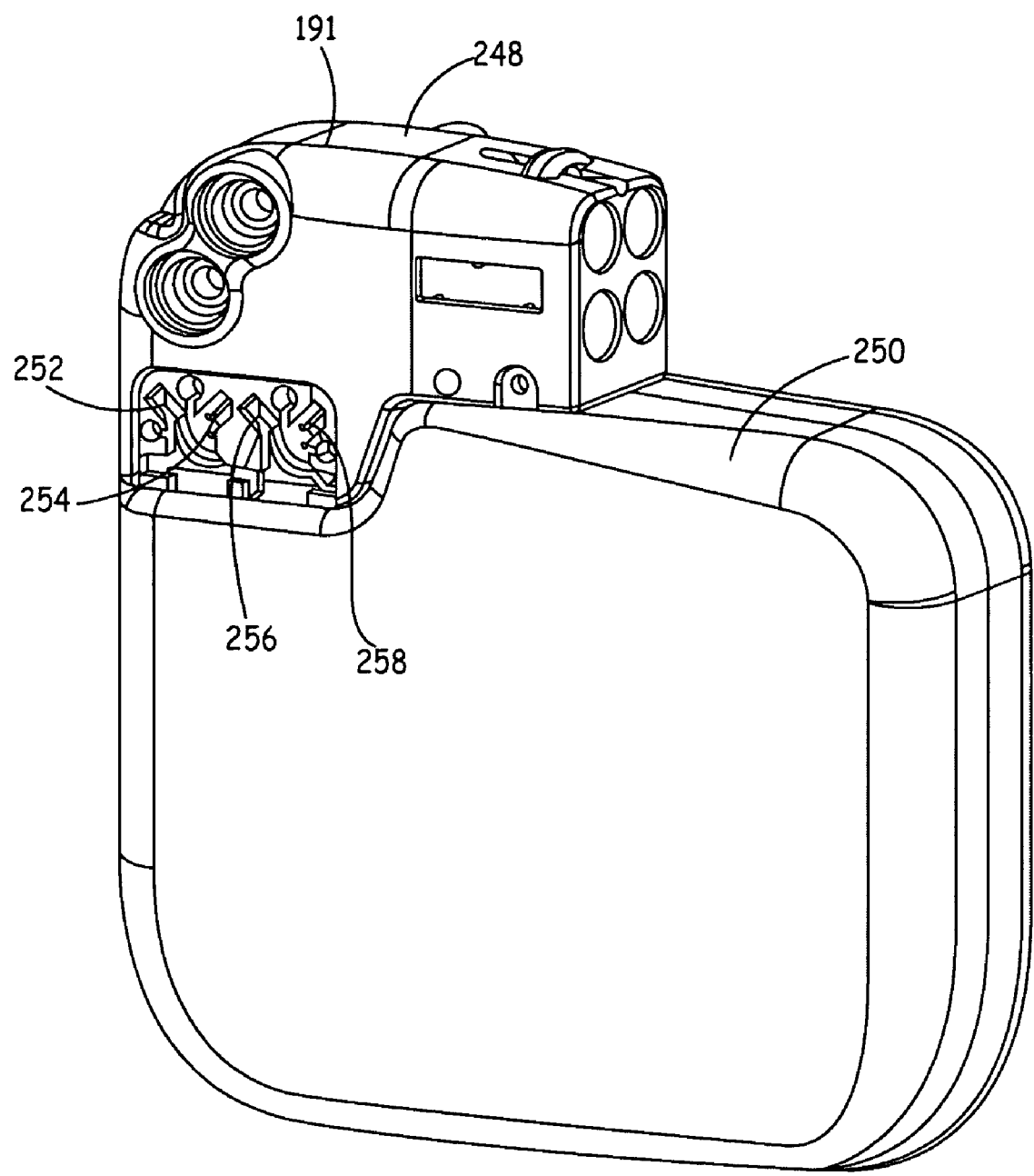
FIG. 14 is a side perspective view of a completed connector assembly coupled to an implantable medical device (IMD).

FIG. 14 is a side perspective view of a completed connector assembly 248 which is similar to that shown in FIG. 11. Connector assembly 248 is coupled to an implantable medical device (IMD) 250, which may be a pacemaker, cardio/defibrillator, neurological pain stimulator, or any other type of implantable medical device utilizing medical electrical leads. In one embodiment, the connector pads such as pads 252 through 258 of the connector assembly 248 are welded or soldered to a feedthrough pattern of the IMD. This provides the desired electrical connections between the connector assembly and the IMD.

Although the above description discusses a particular type of connector assembly adapted to couple to four leads having particular types of connectors, it may be noted that the inventive process may be adapted to manufacture any type of connector assembly having any number of shapes and sizes, and that is adapted to couple to any type of lead connector. Alternatively, the process could be utilized to manufacture any other type of thermoplastic component that is adapted to include conductive piece parts. Thus, the description of the specific connector assembly set forth above should be considered merely exemplary in nature.

What is claimed is:

1. A connector assembly adapted to be implanted within a living body, comprising:
   a core element formed of a first thermoplastic material, the core element forming a plurality of positioning structures extending therethrough;
   a plurality of conductive members integrally positioned along the core element;
   a plurality of electrically conductive circuit elements extending through the plurality of positioning structures from a first end electrically coupled to the plurality of conductive members and a second end extending outward from the core element at the plurality of positioning structures; and
   an overmold structure formed of a second thermoplastic material, the overmold structure extending over and adhering to the core element and at least a portion of the plurality of circuit members.

2. The connector assembly of claim 1, wherein the overmold structure extends over and adheres to the first end of the plurality of circuit elements and a portion of the plurality of circuit elements extending between the plurality of positioning structures and the second end.

3. The connector assembly of claim 1, wherein a surface of the core element includes predetermined ridge members to enhance the bonding of the core element to the overmold structure.

4. The connector assembly of claim 1, wherein the core element includes a groove member to receive at least a portion of the plurality of circuit elements.

5. The connector assembly of claim 1, wherein the core element includes forms a plurality of receptacles adapted to receive the plurality of conductive members.

6. The connector assembly of claim 1, wherein the plurality of conductive members are selected from the group consisting of a set-screw block and a connector member.

7. The connector assembly of claim 1, wherein the plurality of circuit elements are mechanically coupled.

8. The connector assembly of claim 1, wherein the plurality of circuit elements include connector pads positioned along the second end to be coupled to an implantable medical device.

9. The connector assembly of claim 1, wherein the first and the second thermoplastic materials are each selected from the group consisting of polyurethane and polysulfone.

10. The connector assembly of claim 1, wherein the core element is formed using an injection mold process.

11. The connector assembly of claim 1, wherein the core element is formed using a machining process.

12. The connector assembly of claim 1, wherein the mass of the core element is less than fifty percent of the mass of the overmold structure.

13. The connector assembly of claim 1, wherein the plurality of positioning structures include apertures.

14. The connector assembly of claim 1, wherein the plurality of positioning structures include channels positioned along an outer surface of the core member.

15. A connector assembly adapted to be implanted within a living body, comprising:
    a core element formed of a first thermoplastic material, the core element forming a plurality of receptacles and a plurality of positioning structures extending therethrough;
    a plurality of conductive members integrally positioned along the core element within the plurality of receptacles;
    a plurality of electrically conductive circuit elements extending through the plurality of positioning structures from a first end electrically coupled to the plurality of conductive members and a second end extending outward from the core element at the plurality of positioning structures; and
    an overmold structure formed of a second thermoplastic material, the overmold structure extending over and adhering to the core element, the first end of the plurality of circuit elements, and a portion of the plurality of circuit elements extending between the plurality of positioning structures and the second end.

16. The connector assembly of claim 15, wherein a surface of the core element includes predetermined ridge members to enhance the bonding of the core element to the overmold structure.

17. The connector assembly of claim 15, wherein the core element includes a groove member to receive at least a portion of the plurality of circuit elements.

18. The connector assembly of claim 15, wherein the plurality of conductive members are selected from the group consisting of a set-screw block and a connector member.

19. The connector assembly of claim 15, wherein the plurality of circuit elements are mechanically coupled.

20. The connector assembly of claim 15, wherein the plurality of circuit elements include connector pads positioned along the second end to be coupled to an implantable medical device.

21. The connector assembly of claim 15, wherein the first and the second thermoplastic materials are each selected from the group consisting of polyurethane and polysulfone.

22. The connector assembly of claim 15, wherein the core element is formed using an injection mold process.

23. The connector assembly of claim 15, wherein the core element is formed using a machining process.

24. The connector assembly of claim 15, wherein the mass of the core element is less than fifty percent of the mass of the overmold structure.

25. The connector assembly of claim 15, wherein the plurality of positioning structures include apertures.

26. The connector assembly of claim 15, wherein the plurality of positioning structures include channels positioned along an outer surface of the core member.

* * * * *